United States Patent [19]

Yoshimoto et al.

[11] 4,277,624
[45] Jul. 7, 1981

[54] PROCESS FOR PREPARING DIPHENYL ETHERS

[75] Inventors: Takeo Yoshimoto, Yokohama; Keiichi Igarashi, Musashino; Kengo Oda; Masaaki Ura, both of Yokohama; Naoki Sato, Kamakura, all of Japan

[73] Assignee: Mitsui Toatsu Chemicals, Inc., Tokyo, Japan

[21] Appl. No.: 54,865

[22] Filed: Jul. 5, 1979

[30] Foreign Application Priority Data

Jul. 5, 1978 [JP] Japan .................................. 53-80860

[51] Int. Cl.³ ..................... C07C 41/00; C07C 148/00
[52] U.S. Cl. ........................................ 568/44; 568/62; 568/586; 560/17; 71/98; 71/121; 71/124; 564/430
[58] Field of Search .......................... 568/586, 44, 62; 560/17

[56] References Cited

U.S. PATENT DOCUMENTS

| | | |
|---|---|---|
| 2,988,571 | 6/1961 | MacFie et al. . |
| 3,294,847 | 12/1966 | Albright et al. . |
| 3,376,281 | 4/1968 | Cox et al. . |
| 3,562,335 | 2/1971 | Gildersleve . |
| 3,776,961 | 12/1973 | Theisseu . |
| 3,798,276 | 3/1974 | Bayer et al. . |
| 3,849,503 | 11/1974 | Shigehara et al. . |
| 3,928,416 | 12/1975 | Bayer et al. . |
| 3,969,102 | 7/1976 | Yoshimoto et al. . |
| 4,062,896 | 12/1977 | Yoshimoto et al. .................. 568/586 |
| 4,093,446 | 6/1978 | Bayer et al. ..................... 568/586 X |

FOREIGN PATENT DOCUMENTS

| | | |
|---|---|---|
| 45-28198 | 9/1970 | Japan . |
| 49-236 | 1/1974 | Japan . |
| 50-37740 | 4/1975 | Japan . |
| 51-79721 | 7/1976 | Japan . |

Primary Examiner—Bernard Helfin
Attorney, Agent, or Firm—Fisher, Christen & Sabol

[57] ABSTRACT

Novel diphenyl ether compounds of the general formula:

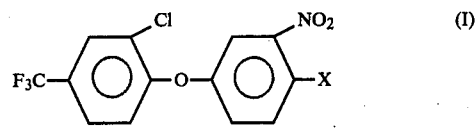

(I)

wherein X represents a hydrogen atom or a nitro group, process for preparing the same and diphenyl ethers of the general formula:

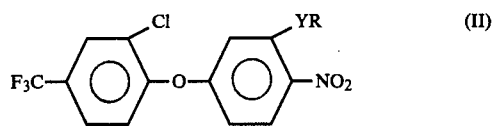

(II)

wherein R represents a hydrogen atom, or substituted or unsubstituted alkyl group, alkenyl group or alkynyl group, and Y represents an oxygen atom, a sulfur atom, or the group

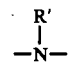

wherein R' is defined as R above, by reacting 2-chloro-4-trifluoromethylphenyl-3,4-dinitrophenyl ether with a compound of the general formula:

RYH             (III)

wherein R and Y have the same meanings as defined above, respectively. The latter diphenyl ether compounds of the general formula (II) are useful as herbicides.

9 Claims, No Drawings

PROCESS FOR PREPARING DIPHENYL ETHERS

BACKGROUND OF THE INVENTION

This invention relates to diphenyl ether compounds expressed by the general formula

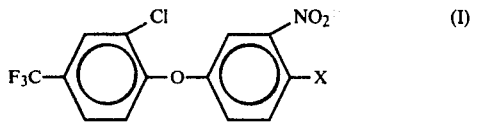

wherein X represents a hydrogen atom or a nitro group, and also to a process for preparing the same and diphenyl ethers expressed by the general formula

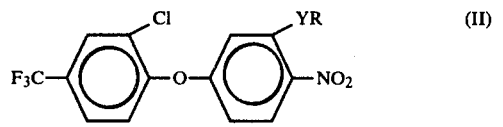

wherein R represents a hydrogen atom, or substituted or unsubstituted alkyl group, alkenyl group or alkynyl group, and Y represents an oxygen atom, a sulfur atom, a nitrogen atom or an imino group, characterized by reacting 2-chloro-4-trifluoromethylphenyl-3,4-dinitrophenyl ether with a compound expressed by the general formula

RYH    (III)

wherein R and Y have the same meanings as defined above, respectively.

A number of compounds as expressed by the general formula (II) are known to show the excellent herbicidal activity.

For instance, Japanese Laid-Open patent application Nos. 49-236, 50-37740 and 51-79721 deal with processes of preparing compounds of the just-mentioned type. Then, reference is made particularly to the process of the invention, so as to illustrate the preparation of the compounds expressed by the foregoing general formula (II).

(A) Preparation Process Described in Japanese Laid-Open Patent Application No. 49-236

2,4-Bis(2-chloro-4-trifluoromethylphenoxy)benzene is obtained by condensation reaction of 3,4-dichlorobenztrifluoride with resorcinol and then nitrated to give 2,4-bis(2-chloro-4-trifluoromethylphenoxy)nitrobenzene. The nitrated product is reacted with alcohols, thiols or amines under alkaline conditions to allow interchange reaction of the phenoxy group in ortho position to the nitro group, whereby an intended compound is obtained.

(B) Preparation Process Described in Japanese Laid-Open Patent Application No. 50-37740

2-Chloro-4-trifluoromethylphenyl-3-chlorophenyl ether is obtained by condensation reaction of 3,4-dichlorobenztrifluoride with metachlorophenol and then nitrated to give 2-chloro-4-trifluoromethylphenyl-3-chloro-4-nitrophenyl ether. The nitrated product is reacted with thiols under alkaline conditions to allow interchange reaction of the chlorine atom in ortho position to the nitro group, whereby an intended compound is obtained.

The two production processes which are considered to be the prior art of the invention have been described but these processes are not satisfactory and involve various problems to be solved. The process (A), for instance, requires 2 moles of 3,4-dichlorobenztrifluoride to obtain one mole of the active compound. In order to effectively utilize the starting compounds, the 2-chloro-4-trifluoromethylphenol produced in the final interchange reaction must be recovered for reuse, which results in complicate reaction process and increased production cost.

With the process (B), on the other hand, the nitration reaction of 2-chloro-4-trifluoromethylphenyl-3-chlorophenyl ether inevitably involves contamination of the intended product with its isomer of 2-chloro-4-trifluoromethylphenyl-2-nitro-5-chlorophenyl ether. In addition, since the 2-chloro-4-trifluoromethylphenyl-3-chloro-4-nitrophenyl ether product remains liquid at a normal temperature, it is difficult to separate the isomer having a very similar properties from the product, thus lowering the purity of a final product.

OBJECT OF THE INVENTION

It is therefore an object of this invention to provide a novel diphenyl ether compound which is used as an intermediate in preparing herbicides.

It is another object of the present invention to provide a process for preparing the above-mentioned novel diphenyl ether.

It is further object of the invention to provide a process for preparing a diphenyl ether compound possessing a herbicidal activity, in high purity and in high yield, by using the above-mentioned novel diphenyl ether compound as an intermediate.

Other and another objects, features and advantages of the present invention will become more apparent from the following description.

DETAILED DESCRIPTION OF THE INVENTION

We have made the intensive studies to develop a process of preparing the compounds of the formula (II) which overcomes the disadvantages of the prior art processes and found that the compound of the formula (II) can be produced in high purity and in high yield when using as a starting material 2-chloro-4-trifluoromethylphenyl-3,4-dinitrophenyl ether (Compound 1) which is prepared in high yield by nitration of 2-chloro-4-trifluoromethylphenyl-3-nitrophenyl ether (Compound 2).

Broadly, the Compound 1 of the general formula (I) and the Compound 2 are prepared as follows: m-nitrophenol and 3,4-dichlorobenztrifluoride are interacted in the presence of a deacidifying agent such as sodium hydroxide or potassium carbonate in solvent-free condition or in a polar solvent such as, for example, sulforan at 100°–290° C., preferably 140°–220° C. and most preferably 170°–180° C. for 4–7 hours to produce the Compound 2. The Compound 2 is then nitrated by a conventional method to give Compound 1 with high selectivity. The thus obtained Compound 1 is highly crystalline and may be readily purified by recrystallization but stands for the purpose of the invention even though it is left as crude crystals. By the use of the Compound 1, the compound of the general formula (II) is easily produced by reacting the Compound 1 with alcohols, thiols or amines in the presence of an alkali.

The alcohols mean compounds having a hydroxyl group and including, for example, alkyl alcohols such as methanol, ethanol, and the like, unsaturated alcohols such as allyl alcohol and propargyl alcohol, halogenated or other substituted alcohols such as fluoroethanol. The thiols mean compounds having a mercapto group, including hydrogen sulfide. The amines are primary and secondary amines or ammonia. The useful alkalis are alkali metal hydroxides such as sodium hydroxide, potassium hydroxide and the like, or alkali metal salts such as the above-mentioned alcohols and thiols. The reaction solvents are alcohols or thiols mentioned above or compounds which are stable under the alkaline conditions. Preferably, dioxane or tetrahydrofuran is used. When a tertiary alcohol such as tert-butanol is used as the solvent, the tertiary alcohol is not involved in the reaction for obtaining Compound 11 (Example 4).

The preparation of the compounds expressed by the general formula (I) and (II) will be particularly illustrated in the following examples. The Compound Numbers in the Examples are referred to in Tables 1 and 2 appearing hereinafter.

EXAMPLE 1

Preparation of 2-chloro-4-trifluoromethyl-phenyl-3,4-dinitrophenyl ether (Compound 1)

16.7 g of m-nitrophenol, 16.6 g of potassium carbonate and 150 ml of sulforan were mixed and agitated. To the mixture was gradually added 31.0 g of 3,4-dichlorobenztrifluoride, followed by heating for reaction at 170°–180° C. for 6 hours. After cooling the reaction solution was charged into water and the precipitated oil layer was extracted with benzene. The benzene extract was washed with water, dried with anhydrous sodium sulfate, followed by distilling off the solvent under reduced pressure to obtain a crude product. This crude product was distilled under reduced pressure to obtain 33.8 g (yield 88.8%) of 2-chloro-4-trifluoromethylphenyl-3-nitrophenyl ether (Compound 2). 31.7 g of the thus obtained 2-chloro-4-trifluoromethylphenyl-3-nitrophenyl ether was dissolved in 50 ml of acetic anhydride, into which was dropped a separately prepared mixed acid (obtained by mixing 8 g of fuming nitric acid (specific density 1.5) and 30 ml of 95% sulfuric acid) over about 3 hours while maintaining the solution at 5°–10° C. After the dropping, the mixture was agitated at room temperature for further 2 hours to complete the reaction, after which the reaction solution was charged into water and extracted with benzene. The benzene extract was washed with water, dried, and evaporated to dryness under reduced pressure, followed by recrystallizing from ethanol to obtain 33 g of Compound 1 (yield 91.0%).

EXAMPLE 2

Preparation of 2-chloro-4-trifluoromethyl-phenyl-3-ethoxy-4-nitrophenyl ether (Compound 3)

36 g of the Compound 1 was dissolved in 50 ml of dioxane. To this solution was added a solution of 6 g potassium hydroxide in 20 ml of ethanol while maintaining the temperature at 30°–40° C. Thereafter the mixture was agitated at 40° C. for 3 hours to complete the reaction and then charged into water. The resulting crystals were collected by filtration, and washed sufficiently with water to obtain 34.5 g of crude crystals of Compound 3 (yield 96%).

The thus obtained crude crystals were recrystallized from ethanol to obtain 31 g (yield 86%) of pure crystals.

EXAMPLE 3

Preparation of 2-chloro-4-trifluoromethyl-phenyl-3-fluoroethoxy-4-nitrophenyl ether (Compound 4)

14 g of the Compound 1 was dissolved in 20 ml of dioxane. To this solution were added 2.5 g of powdered potassium hydroxide and 3 g of 2-fluoroethanol, followed by agitating at 60°–70° C. for 3 hours. After completion of the reaction, the solution was cooled to room temperature and charged into water. The resulting crystals were collected by filtration and washed with water to obtain 14 g (yield 95.6%) of crude crystals. The crude crystals were recrystallized from ethanol to obtain 12 g of pure crystals (with a yield of 82%).

Compounds 5–10 were also obtained similarly to the procedure of Example 3 wherein Compound 1 was reacted with corresponding alcohols in the presence of an alkali such as potassium hydroxide or sodium hydroxide.

EXAMPLE 4

Preparation of 2-chloro-4-trifluoromethyl-phenyl-3-hydroxy-4-nitrophenyl ether (Compound 11)

18 g of Compound 1, 50 ml of tert-butanol and 3 g of potassium hydroxide were mixed and agitated at 70° C. for 3 hours. After completion of the reaction, the solution was cooled to room temperature and the resulting red crystals were collected by filtration and washed with a small amount of water and then with benzene. The thus obtained crystals were dissolved in 100 ml of acetone. To this solution was added 400 ml of water to give a uniform solution. Thereafter, hydrochloric acid was added to render the solution acidic. The resulting crystals were collected by filtration and washed sufficiently with water to obtain 16 g of crude crystals. The crystals were recrystallized from a mixed solvent of benzene and hexane to obtain 13 g (yield 81%) of a pure product of Compound 11.

EXAMPLE 5

Preparation of 2-chloro-4-trifluoromethyl-phenyl-3-methylthio-4-nitrophenyl ether (Compound 13)

3.6 g of Compound 1 was dissolved in 20 ml of dioxane. To this solution was added 1.5 g of sodium methylmercaptide, followed by agitating at room temperature for 2 hours and charging into water. The resulting crystals were collected by filtration, washed well with water and recrystallized from ethanol to obtain 3 g (yield 86%) of Compound 13.

The preparation of Compound 14 is omitted since this compound can be prepared similarly to the case of Example 5 using a different starting material.

EXAMPLE 6

Preparation of 2-chloro-4-trifluoromethyl-phenyl-3-mercapto-4-nitrophenyl ether (Compound 12)

18 g of Compound 1 was dissolved in 100 ml of tetrahydrofuran. To this solution was dropped 200 ml of a sodium hydrosulfide solution* over 1 hour in a stream of nitrogen gas. After the dropping, the solution was agitated for further 4 hours at room temperature, to which was added dilute hydrochloric acid while ice-cooling unit it became slightly acidic. Nitrogen gas was violently injected into the solution to expel the liberated hydrogen sulfide, followed by extraction with benzene. The benzene extract was washed with water, dried and treated under reduced pressure to distill off the solvent. Then it was purified by a chromatography using a silica gel column (solvent: benzene/hexane=1/1) to obtain 15 g of Compound 12 (yield 87%).

*Sodium hydrosulfide solution: Prepared according to the method described in J. Chem. Soc., 242 (1948). That is, 40 g of sodium hydrosulfide ($Na_2S.9H_2O$) was dissolved in 100 ml of water. To this solution was portion by portion added 14 g of sodium bicarbonate at room temperature. After complete and homogenous dissolution, 100 ml of methanol was added to the solution. Afterh ageing for 30 minutes, the resulting sodium carbonate precipitate was removed by filtration and washed with 50 ml of methanol. The filtrate and the wash were mixed for use as a sodium hydrosulfide solution.

The physical characteristics of the compounds obtained in Example 1 are shown in Table 1 and the compounds prepared by the procedures of Example 2–7 and their physical characteristics are shown in Table 2.

TABLE 1

| | Compound of General Formula (I) | | | | | |
|---|---|---|---|---|---|---|
| Compound No. | Substituent X | Melting Point (Boiling Point) °C. | \multicolumn{4}{c}{Elementary Analysis (%) Found/ (Calculated)} |
| | | | C | H | N | Cl | F |
| 1 | $NO_2$ | 81–82 | 43.32 | 1.73 | 7.71 | 9.65 | 15.63 |
| | | | (43.05 | 1.67 | 7.73 | 9.78 | 15.72) |
| 2 | H | 150–155/0.2 mm Hg | 48.96 | 2.08 | 4.48 | 11.23 | 17.35 |
| | | | (49.15 | 2.22 | 4.41 | 11.16 | 17.94) |

TABLE 2

| | Compounds of General Formula (II) | | | | | | | |
|---|---|---|---|---|---|---|---|---|
| Compound No. | Substituent of Formula (II) Y | R | Melting Point °C. | \multicolumn{5}{c}{Elementary Analysis (%) Found/(Calculated)} |
| | | | | C | H | N | Cl | F | S |
| 3 | O | $-CH_2CH_3$ | 85–86 | 50.03 | 3.26 | 3.58 | 10.05 | 15.66 | |
| | | | | (49.81 | 3.07 | 3.82 | 9.80 | 15.76 | —) |
| 4 | O | $-CH_2CH_2F$ | 99–100 | 47.40 | 2.61 | 3.64 | 9.16 | 19.58 | |
| | | | | (47.45 | 2.65 | 3.69 | 9.34 | 19.49 | —) |
| 5 | O | $-CH_2CH=CH_2$ | 77.5–79 | 51.75 | 2.78 | 3.99 | 9.67 | 15.38 | |
| | | | | (51.42 | 2.97 | 3.75 | 9.49 | 15.25 | —) |
| 6 | O | $-CH_2.C\equiv CH$ | 88–90 | 51.65 | 2.31 | 3.58 | 9.38 | 15.54 | |
| | | | | (51.70 | 2.44 | 3.77 | 9.54 | 15.33 | —) |
| 7 | O | $-CH(CH_3)_2$ | 49.5–51 | 50.93 | 3.44 | 3.89 | 9.66 | 13.52 | |
| | | | | (51.14 | 3.49 | 3.73 | 9.44 | 13.31 | —) |
| 8 | O | $-CH_2CH-CH_2$ (epoxide) | 49–53 | 49.25 | 2.75 | 3.41 | 9.06 | 14.33 | |
| | | | | (49.31 | 2.85 | 3.59 | 9.10 | 14.63 | —) |
| 9 | O | $-CH_2CH_2OC_2H_5$ | 62–64 | 50.31 | 3.69 | 3.42 | 8.71 | 14.08 | |
| | | | | (50.32 | 3.73 | 3.45 | 8.74 | 14.05 | —) |
| 10 | O | $-CH_2CH_2SCH_3$ | 42–45 | 47.21 | 3.19 | 3.47 | 8.52 | 14.11 | 7.63 |
| | | | | (47.12 | 3.21 | 3.44 | 8.69 | 13.98 | 7.86) |
| 11 | O | $-H$ | 71.1–72.6 | 46.71 | 2.08 | 4.15 | 10.55 | 17.25 | |
| | | | | (46.79 | 2.11 | 4.20 | 10.63 | 17.08 | —) |
| 12 | S | $-H$ | 80–81.5 | 44.75 | 2.05 | 4.03 | 10.05 | 15.96 | 9.45 |
| | | | | (44.64 | 2.02 | 4.01 | 10.14 | 16.30 | 9.17) |
| 13 | S | $-CH_3$ | 94–95 | 42.88 | 1.93 | 3.81 | 9.66 | 15.63 | 8.75 |
| | | | | (42.92 | 1.94 | 3.85 | 9.75 | 15.67 | 8.82) |
| 14 | S | $-CH_2COOC_2H_5$ | 71.5–72.5 | 46.93 | 2.95 | 3.16 | 8.07 | 13.13 | 7.22 |
| | | | | (46.85 | 3.01 | 3.21 | 8.14 | 13.08 | 7.36) |
| 15 | $\overset{H}{\underset{N}{\mid}}$ | $-H$ | 85.5–87.5 | 46.87 | 2.28 | 8.51 | 10.43 | 17.05 | — |
| | | | | (46.93 | 2.42 | 8.42 | 10.66 | 17.13 | —) |
| 16 | $\overset{H}{\underset{N}{\mid}}$ | $-CH_2CH_2CH_3$ | 88–89 | 51.12 | 3.77 | 7.45 | 9.63 | 14.99 | — |
| | | | | (51.28 | 3.77 | 7.48 | 9.46 | 15.21 | —) |

EXAMPLE 7

Preparation of 2-chloro-4-trifluoromethyl-phenyl-3-propylamino-4-nitrophenyl ether (Compound 16)

11 g of Compound 1 was dissolved in 50 ml of dioxane. To this solution was added 5 g of n-propylamine, followed by agitating for reaction at 60° C. for 3 hours. After completion of the reaction, the reaction solution was cooled to room temperature and charged into water. The resulting solid precipitate was separated by filtration and air-dried to obtain a crude product (quantitatively). The crude product was sufficiently powdered and washed with n-hexane of 40°–50° C. to obtain 10.2 g (yield 89%) of an intended yellow product.

Compound 15 was prepared in the same manner as in Example 7 where a dioxane solution of Compound 1 was heated to 50°–60° C., into which ammonia gas was introduced for reaction.

What is claimed is:

1. A process for preparing a diphenyl ether compound expressed by the general formula:

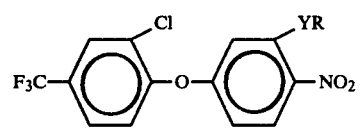

wherein R represents a hydrogen atom, or substituted or unsubstituted alkyl group, alkenyl group or alkynyl group, and Y represents an oxygen atom or a sulfur atom, comprising reacting 2-chloro-4-trifluoromethyl-phenyl-3,4-dinitrophenyl ether:

(a) with an alkali metal hydroxide, or with an alcohol selected from the group consisting of substituted or unsubstituted alkyl alcohols, alkenyl alcohols and alkynyl alcohols in the presence of an alkali metal hydroxide, or with an alkali metal salt of an alcohol as defined above, when Y is oxygen, or (b) with an alkali metal hydrosulfide, or with a thiol selected from the group consisting of substituted or unsubstituted alkyl thiols, alkenyl thiols and alkynyl thiols in the presence of an alkali metal hydroxide, or with an alkali metal salt of a thiol as defined above, when Y is sulfur.

2. A process as claimed in claim 1 wherein said alkali metal hydroxide is selected from the group consisting of sodium hydroxide, and potassium hydroxide, said alcohol is selected from the group consisting of methanol, ethanol, allyl alcohol, propargyl alcohol, fluoroethanol, isopropyl alcohol, 3-hydroxypropylene oxide, 2-hydroxydiethyl ether, and methylthioethanol, said thiol is selected from the group consisting of methyl mercaptan and ethoxycarbonylmethyl mercaptan, and said alkali metal hydrosulfide is sodium hydrosulfide.

3. A process as claimed in claim 1 wherein said reaction is in an organic solvent selected from the group consisting of dioxane, tetrahydrofuran, and tert-butanol.

4. A process as claimed in claim 1 wherein said reaction is with said alcohol in the presence of an alkali metal hydroxide.

5. A process as claimed in claim 1 wherein said reaction is with said alkali metal salt of an alcohol as defined above.

6. A process as claimed in claim 1 wherein said reaction is with said thiol in the presence of an alkali metal hydroxide.

7. A process as claimed in claim 1 wherein said reaction is with an alkali metal salt of said thiol.

8. A process as claimed in claim 1 wherein R is hydrogen and said reaction of said dinitrophenyl ether is with an alkali metal hydroxide or an alkali metal hydrosulfide.

9. A process as claimed in claim 8 wherein said reaction is with an alkali metal hydroxide.

* * * * *